(12) United States Patent
Leij

(10) Patent No.: US 8,008,553 B2
(45) Date of Patent: Aug. 30, 2011

(54) SWEET PEPPER LINE SBY28-1223

(75) Inventor: Jurko Leij, Gouda (NL)

(73) Assignee: Seminis Vegetable Seeds, Inc., Woodland, CA (US)

( * ) Notice: Subject to any disclaimer, the term of this patent is extended or adjusted under 35 U.S.C. 154(b) by 506 days.

(21) Appl. No.: 12/183,753

(22) Filed: Jul. 31, 2008

(65) Prior Publication Data

US 2010/0031386 A1    Feb. 4, 2010

(51) Int. Cl.
*A01H 5/00* (2006.01)
*A01H 5/10* (2006.01)
*A01H 1/02* (2006.01)
*C12N 5/04* (2006.01)

(52) U.S. Cl. .............. 800/317.1; 800/267; 800/260; 800/278; 435/421; 435/430

(58) Field of Classification Search ............. None
See application file for complete search history.

(56) References Cited

U.S. PATENT DOCUMENTS

| | | | | |
|---|---|---|---|---|
| 5,262,316 | A | 11/1993 | Engler et al. | 435/172.3 |
| 7,087,819 | B2 | 8/2006 | Edwards | 800/317.1 |
| 2009/0064369 | A1 | 3/2009 | Berke | 800/317.1 |
| 2009/0064370 | A1 | 3/2009 | Berke | 800/317.1 |
| 2009/0210965 | A1 | 8/2009 | McCarthy | 800/317.1 |
| 2010/0011457 | A1 | 1/2010 | Leij | 800/317.1 |
| 2010/0011458 | A1 | 1/2010 | Leij | 800/317.1 |
| 2010/0115656 | A1 | 5/2010 | McCarthy | 800/317.1 |

OTHER PUBLICATIONS

PAPRYKA. PI 639641 (deposited Jan. 2000).*
Matsunaga et al. Journal of the Japanese Society of Horticultural Science 72(3): 218-220 (2003).*
Boiteux, L. Theoretical and Applied Genetics 90(1): 146-149 (Jan. 1995).*
Application for Community Plant Variety Right, for Pepper (*Casicum annuum L.*) Variety BS 09927864, dated Nov. 19, 2008, European Union.
Berke, "Hybrid seed production in *Capsicum*," *J. of New Seeds*, 1(3/4):49-67, 1999.
Chae et al., "Development of resistant pepper lines against anthracnose using interspecific crossing between *Capsicum baccaturm* and *C. annuum*," *Capsicum & Eggplant Newsletter*, 22:121-124, 2003.
Panda et al., "Cytomorphology of induced octoploid chili pepper (*Capsicum annuum L.*)," *Theor. Appl. Gene.*, 68(6):567-577, 1984.
U.S. Appl. No. 12/183,746, filed Jul. 31, 2008, Leij.
U.S. Appl. No. 12/183,759, filed Jul. 31, 2008, Leij.
U.S. Appl. No. 12/201,233, filed Aug. 29, 2008, Berke.
U.S. Appl. No. 12/201,234, filed Aug. 29, 2008, Berke.
U.S. Appl. No. 12/370,502, filed Feb. 12, 2009, McCarthy.
Pickersgill et al., "Genetic resources and breeding of *Capsicum* ssp.," *Euphytica*, 96:129-133, 1997.
Plant Breeders' Rights Application for Pepper (*Capsicum annuum*) Variety BS 09927864, dated Dec. 21, 2007, The Netherlands.
U.S. PVP Application for Sweet Pepper (*Capsicum annuum L.*) Variety SBY281223, dated Apr. 29, 2009.

* cited by examiner

*Primary Examiner* — David T Fox

(74) *Attorney, Agent, or Firm* — Alissa Eagle, Esq.; SNR Denton US LLP

(57) ABSTRACT

The invention provides seed and plants of the pepper line designated SBY28-1223. The invention thus relates to the plants, seeds and tissue cultures of pepper line SBY28-1223, and to methods for producing a pepper plant produced by crossing a plant of pepper line SBY28-1223 with itself or with another pepper plant, such as a plant of another line. The invention further relates to seeds and plants produced by such crossing. The invention further relates to parts of a plant of pepper line SBY28-1223, including the fruit and gametes of such plants.

24 Claims, No Drawings

SWEET PEPPER LINE SBY28-1223

FIELD OF THE INVENTION

The present invention relates to the field of plant breeding and, more specifically, to the development of pepper line SBY28-1223.

BACKGROUND OF THE INVENTION

The goal of vegetable breeding is to combine various desirable traits in a single variety/hybrid. Such desirable traits may include greater yield, resistance to insects or pests, tolerance to heat and drought, better agronomic quality, higher nutritional value, growth rate and fruit properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform lines requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop which has been subject to such breeding programs and is of particular value is the pepper, which includes bell peppers. *C. annuum* is a herbaceous annual. The plant has a densely branched stem and grows to 1.5 to 5 feet in height. The fruit is green when unripe, then usually changing to red or brown. The species can grow in many climates; however, they thrive in warm and dry climates. Hybrid vigor has been documented in peppers, and hybrids are gaining increasing popularity among farmers throughout the world, especially in countries with plentiful labor (Berke, 1999).

SUMMARY OF THE INVENTION

In one aspect, the present invention provides a pepper plant of the line designated SBY28-1223. Also provided are pepper plants having all the physiological and morphological characteristics of the pepper line designated SBY28-1223. Parts of the pepper plant of the present invention are also provided, for example, including pollen, an ovule, scion, a rootstock, a fruit, and a cell of the plant.

The invention also concerns the seed of pepper line SBY28-1223. The pepper seeds of the invention may be provided as an essentially homogeneous population of pepper seed of the line designated SBY28-1223. Essentially homogeneous populations of seed are generally free from substantial numbers of other seed. Therefore, seed may be defined as forming at least about 97% of the total seed, including at least about 98%, 99% or more of the seed. The population of pepper seed may be particularly defined as being essentially free from hybrid seed. The seed population may be an essentially homogeneous population of seed of the pepper plant designated SBY28-1223.

In another aspect of the invention, a plant of pepper line SBY28-1223 comprising an added heritable trait is provided. The heritable trait may comprise a genetic locus that is, for example, a dominant or recessive allele. In one embodiment of the invention, a plant of pepper line SBY28-1223 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a pepper plant of line SBY28-1223 is provided. The tissue culture will preferably be capable of regenerating pepper plants capable of expressing all of the physiological and morphological characteristics of the line, and of regenerating plants having substantially the same genotype as other plants of the line. Examples of some of the physiological and morphological characteristics of the line SBY28-1223 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides pepper plants regenerated from a tissue culture of the invention, the plants having all the physiological and morphological characteristics of line SBY28-1223.

In yet another aspect of the invention, processes are provided for producing pepper seeds, plants and fruit, which processes generally comprise crossing a first parent pepper plant with a second parent pepper plant, wherein at least one of the first or second parent pepper plants is a plant of the line designated SBY28-1223. These processes may be further exemplified as processes for preparing hybrid pepper seed or plants, wherein a first pepper plant is crossed with a second pepper plant of a different, distinct line to provide a hybrid that has, as one of its parents, the pepper plant line SBY28-1223. In these processes, crossing will result in the production of seed. The seed production occurs regardless of whether the seed is collected or not.

In one embodiment of the invention, the first step in "crossing" comprises planting seeds of a first and second parent pepper plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent pepper plants into plants that bear flowers. A third step may comprise preventing self-pollination of the plants, such as by emasculating the male portions of flowers, (i.e., treating or manipulating the flowers to produce an emasculated parent pepper plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent pepper plants. Yet another step comprises harvesting the seeds from at least one of the parent pepper plants. The harvested seed can be grown to produce a pepper plant or hybrid pepper plant.

The present invention also provides the pepper seeds and plants produced by a process that comprises crossing a first parent pepper plant with a second parent pepper plant, wherein at least one of the first or second parent pepper plants is a plant of the line designated SBY28-1223. In one embodiment of the invention, pepper seed and plants produced by the process are first generation ($F_1$) hybrid pepper seed and plants produced by crossing a plant in accordance with the invention with another, distinct plant. The present invention further contemplates plant parts of such an $F_1$ hybrid pepper plant, and methods of use thereof. Therefore, certain exemplary embodiments of the invention provide an $F_1$ hybrid pepper plant and seed thereof.

In still yet another aspect, the present invention provides a method of producing a plant derived from line SBY28-1223, the method comprising the steps of: (a) preparing a progeny plant derived from line SBY28-1223, wherein said preparing comprises crossing a plant of the line SBY28-1223 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line SBY28-1223. The plant derived from line SBY28-1223 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line SBY28-1223 is obtained which possesses some of the desirable traits of the line as well as potentially other selected traits.

In certain embodiments, the present invention provides a method of producing peppers comprising: (a) obtaining a plant of pepper line SBY28-1223, wherein the plant has been cultivated to maturity, and (b) collecting peppers from the plant.

In still yet another aspect of the invention, the genetic complement of the pepper plant line designated SBY28-1223 is provided. The phrase "genetic complement" is used to refer to the aggregate of nucleotide sequences, the expression of which sequences defines the phenotype of, in the present case, a pepper plant, or a cell or tissue of that plant. A genetic complement thus represents the genetic makeup of a cell, tissue or plant, and a hybrid genetic complement represents the genetic make up of a hybrid cell, tissue or plant. The invention thus provides pepper plant cells that have a genetic complement in accordance with the pepper plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line SBY28-1223 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by pepper plant cells, tissues, plants, and seeds, formed by the combination of a haploid genetic complement of a pepper plant of the invention with a haploid genetic complement of a second pepper plant, preferably, another, distinct pepper plant. In another aspect, the present invention provides a pepper plant regenerated from a tissue culture that comprises a hybrid genetic complement of this invention.

In still yet another aspect, the invention provides a plant of an inbred pepper line that exhibits a combination of traits comprising resistance to Tobamovirus pathotypes P0, P1, P1-2, and P1-2-3, resistance to Tomato Spotted Wilt Virus pathotype P0, large fruits that are orange-yellow in color, and a short, compact plant. In certain embodiments, the combination of traits may be defined as controlled by genetic means for the expression of the combination of traits found in pepper line SBY28-1223.

In still yet another aspect, the invention provides a method of determining the genotype of a plant of pepper line SBY28-1223 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of pepper line SBY28-1223. This line shows uniformity and stability within the limits of environmental influence for the traits described hereinafter. Pepper line SBY28-1223 provides sufficient seed yield. By crossing with a distinct second plant, uniform F1 hybrid progeny can be obtained.

Line SBY28-1223 exhibits a number of improved traits including resistance to Tobamovirus pathotypes P0, P1, P1-2, and P1-2-3, resistance to Tomato Spotted Wilt Virus pathotype P0, large fruits that are orange-yellow in color, and a short, compact plant. The development of the line can be summarized as follows.

A. Origin and Breeding History of Pepper Line SBY28-1223

Year 1, Winter The $F_1$ hybrid SVR 02895310 was made from the parents 992855 and 993128. The parent 992855 was a line with green to yellow maturing bell (LD=0.84) fruits and an open compact plant habit with resistance to Tobamo virus (L4 gene). The parent 993128 was a line with green to red maturing bell fruits (LD=0.90) with a compact plant with resistance to the Tomato spotted wilt virus. Neither parent was marketed directly as open pollinated lines.

Year 2, Winter Plants of the $F_1$ hybrid SVR 02895310 were transplanted into a hybrid trial as stake #00S-467 and allowed to self. SVR 02895310 was tested for Tobamo virus (L4 gene) and Tomato spotted wilt virus resistance and found to be resistant to both. Plant 00S-467-5 was selected and selfed. Plant 00S-467-5 was a compact plant with green fruits which slowly matured to pale red with a LD=0.93. The seeds of 00S-467-5 were designated 20002119.

Year 2, Summer The $F_2$ inbred line 20002119 was planted as stake #00F-2421. Line 20002119 produced compact plants with bell fruits segregating for yellow and red mature color. Line 20002119 was tested for resistance to Tobamo virus (L4 gene) and Tomato spotted wilt virus and found to segregate resistance to both. Individual plants were selected; the seeds of one plant, 00F-2421-8, were designated 20004002.

Year 3, Winter The $F_3$ inbred line 20004002 was planted as stake #01S-2082. Line 20004002 produced plants with green to dark-yellow maturing fruits. Line 200040002 was tested for resistance to Tobamo virus (L4 gene) and Tomato spotted wilt virus and found to be resistant to both. Individual plants were selected; 01S-2082-6 was designated 20013182.

Year 3, Summer The $F_4$ inbred line 20013182 was planted as stake #01F-1102. Line 20013182 produced plants with green to yellow maturing fruits, with a short (LD=0.73) bell shape. The average fruit set was 11 fruits per plant. Line 200013182 was tested for resistance to Tobamo virus (L4 gene) and Tomato spotted wilt virus and was found to be resistant to both viruses. Individual plants were selected; 01F-1102-7 was designated 20014091.

Year 4, Winter The $F_5$ inbred line 20014091 was planted as stake #02S-857. Line 20014091 produced plants with green to yellow maturing fruits, with a short (LD=0.80) bell shape. The average fruit set was 14 fruits per plant. Line 200014091 was tested for resistance to Tobamo virus (L4 gene) and Tomato spotted wilt virus and was found to be resistant to both viruses. Individual plants were selected; 02S-857-2 was designated 20021382.

Year 4, Summer The $F_6$ inbred line 20021382 was planted as stake #02F-318. Line 20021382 produced plants with green to dark yellow slowly maturing fruits, with a short (LD=0.74) bell shape. The average fruit set was 12 fruits per plant. Line 200021382 was tested for resistance to Tobamo virus (L4 gene) and Tomato spotted wilt virus and was found to be resistant to both viruses. Individual plants were selected; 02F-318-6 was designated 20022602.

Year 5, Winter The $F_7$ inbred line 20022602 was planted as stake #03S-705. Line 20022602 produced plants with green to dark yellow slowly maturing fruits, with a short (LD=0.71) bell shape. The average fruit set was 15 fruits per plant. #03S-705 was evaluated on uniformity, seeds of multiple plants were bulked and designated "SBY28-1223."

Year 5, Summer Planted SBY28-1223. This line produced a concentrated set of large, sweet, square-shaped yellow-orange mature fruit on a short, compact plant. Fruit were rather flat (LD=0.77), very smooth, with a medium shoulder and deep blossom end. The line is resistant to the Tobamo virus (L4 gene) and the Tomato spotted wilt virus.

SBY28-1223 was determined to be uniform and stable within commercially acceptable limits. As is true with other peppers, a small percentage of variants can occur within commercially acceptable limits for almost any characteristic during the course of repeated multiplication. However no variants were observed during the times in which SBY28-1223 was observed in other trials.

B. Physiological and Morphological Characteristics of Pepper Line SBY28-1223

In accordance with one aspect of the present invention, there is provided a plant having the physiological and morphological characteristics of pepper line SBY28-1223. A description of the physiological and morphological characteristics of pepper line SBY28-1223 is presented in Table 1.

TABLE 1

Physiological and Morphological Characteristics of Line SBY28-1223

| CHARACTERISTIC | Pepper Variety SBY 28-1223 |
|---|---|
| 1. Species | *C. annuum* |
| 2. Maturity in region of best adaptability | |
|    Days from transplanting until mature green stage | 55 |
|    Days from transplanting until mature red or yellow stage | 90 |
|    Days from direct seeding until mature green stage | 90 |

TABLE 1-continued

Physiological and Morphological Characteristics of Line SBY28-1223

| CHARACTERISTIC | Pepper Variety SBY 28-1223 |
| --- | --- |
| Days from direct seeding until mature red or yellow stage | 125 |
| 3. Plant | |
| Habit | Compact |
| Attitude | Prostate (Delphin, Trophy) |
| Plant height | 105 cm |
| Plant width | 55 cm |
| Length of stem from cotyledon to first flower | 20 cm |
| Length of the third internode from soil surface | 120 mm |
| Length of stem | Short (Delphin, Trophy) |
| Shortened internode (in upper part) | Absent (California wonder, De Cayenne) |
| Length of internode (on primary side shoots) | Very short (Albaregia) |
| Stem: hairiness of nodes | Weak (Andevalo, Clovis) |
| Height | Very short (Kalocsai 601) |
| Basal branches | Few (2-3) |
| Branch flexibility | Willowy (Cayenne Long Red) |
| Stem strength (breakage resistance) | Inter-mediate |
| 4. Leaf | |
| Length of blade | Medium (Altol, Blondy, Marconi, Merit, Anthea) |
| Width of blade | Medium (Albaregia, Balaton, Danubia, Marconi, Merit) |
| Leaf width | 140 mm |
| Leaf length | 205 mm |
| Petiole length | 90 mm |
| Color | medium green |
| Color (RHS color value chart) | RHS 139A |
| Intensity of green color | medium (Doux très, long des Landes, Merit) |
| Mature leaf shape | Broad elliptic (Solario) |
| Leaf and stem pubescence | moderate |
| Undulation of margin | very weak |
| Blistering | weak (Pusztagold) |
| Profile in cross section | moderately concave (Doux italien, Favolor) |
| Glossiness | medium (Alby, Eolo) |
| Peduncle: attitude | drooping (Heldor, Lamuyo) |
| 5. Flowers | |
| Number of flowers per leaf axil | 1 |
| Number of calyx lobes | 8 |
| Number of petals | 6 |
| Flower diameter | 35 mm |
| Corolla color | white |
| Anther color | purple |
| Style length | same as stamen |
| Self-incompatibility | Absent |
| 6. Fruit | |
| Group | Bell (Yolo Wonder L.) |
| Color (before maturity) | green (California wonder, Lamuyo) |
| Intensity of color (before maturity) | dark |
| Immature fruit color | dark green |
| Immature fruit color (RHS color chart value) | RHS 139 A |
| Attitude/position | drooping/pendent (De Cayenne, Lamuyo) |
| Length | Short (Delphin, Petit carre doux) |
| Diameter | broad (Clovis, Lamuyo) |
| Ratio length/diameter | Medium (Adra, Cherry Sweet, Daniel, Delphin, Edino) |
| Calyx diameter | 38 mm |
| Fruit length | 74 mm |
| Fruit diameter at calyx attachment | 92 mm |
| Fruit diameter at mid-point | 95 mm |
| Flesh thickness at mid-point | 8 mm |

TABLE 1-continued

Physiological and Morphological Characteristics of Line SBY28-1223

| CHARACTERISTIC | Pepper Variety SBY 28-1223 |
|---|---|
| Average number of fruits per plant | 6 |
| % large fruits | 90% |
| % medium fruits | 10% |
| % small fruits | 0% |
| Average fruit weight | 265 gm |
| Shape in longitudinal section | square (Delphin, Yolo Wonder) |
| Shape in cross section (at level of placenta) | circular (Cherry Sweet, Doux très long des Landes) |
| Sinuation of pericarp at basal part | strong (Alfa) |
| Sinuation of pericarp excluding basal part | medium (Ursus) |
| Texture of surface | smooth or very slightly wrinkled (Milord) |
| Color (at maturity) | yellow (Golden calwonder, Heldor) |
| Intensity of color (at maturity) | dark |
| Mature fruit color | orange-yellow |
| Mature fruit color (RHS color chart value) | 17A |
| Glossiness | medium/moderate (Carré doux extra hatif, Lamuyo, Sonar) |
| Stalk cavity | present (Bingor, Lamuyo) |
| Depth of stalk cavity | medium (Lamuyo, Magister) |
| Measurements (pedicel length) | 50 mm |
| Measurements (pedicel thickness) | 13 mm |
| Pedicel shape | curved |
| Pedicel cavity | absent |
| Measurements (depth of pedicel cavity) | 5 mm |
| Base shape | cupped |
| Shape of apex | blunt |
| Shape | Bell (Yolo Wonder L.) |
| Set | Concentrated |
| Depth of interloculary grooves | medium (Clovis, Lamuyo, Marconi) |
| Number of locules | predominantly four and more (Palio, PAZ szentesi) |
| % of fruits with one locule | 0% |
| % of fruits with two locules | 0% |
| % of fruits with three locules | 15% |
| % of fruits with four locules | 85% |
| % fruits with five or more locules | 0% |
| Average number of locules | 4 |
| Thickness of flesh | thick (Andevala, Bingo, Daniel, Topgirl) |
| Calyx: aspect | non-enveloping/saucer-shaped (Lamuyo, Sonar) |
| Pungency | sweet |
| Capsaicin in placenta | absent (Sonar) |
| Flavor | mild pepper flavor |
| Glossiness | moderate |
| 7. Seed | |
| Seed cavity length | 20 mm |
| Seed cavity diameter | 48 mm |
| Placenta length | 30 mm |
| Number of seeds per fruit | 70 |
| Grams per 1000 seeds | 8.5 gm |
| Color | yellow |
| 8. Anthocyanin | |
| Seedling: hypocotyl | weak |
| Stem | moderate |
| Nodes | moderate |
| Intensity of anthocyanin coloration of nodes | strong (Piquant d'Algerie, Zarai) |
| Leaf | weak |
| Pedicel | weak |
| Calyx | absent |
| Anthocyanin coloration in anther | present |
| Beginning of flowering ($1^{st}$ flower on $2^{nd}$ flowering node) | medium (Lamuyo, Latino) |
| Time of maturity | late (Daniel, Doux d'Espagne) |
| 9. Disease Resistance | |
| Resistance to Tobamovirus Pathotype 0 (Tobacco Mosaic Virus (0)) | present/most resistant (Lamuyo, Sonar, Yolo Wonder) |
| Resistance to Tobamovirus Pathotype 1-2 (Tomato Mosaic Virus (1-2)) | present (Delgado, Festos, Novi, Orion) |
| Resistance to Tobamovirus Pathotype 1-2-3 (Pepper Mild Mottle Virus (1-2-3)) | present/most resistant (Cuby, Tasty) |
| Resistance to Curly Top Virus | most susceptible |
| Resistance to Potato Virus Y (PVY) | most susceptible |
| Resistance to PVY Pathotype 0 | absent (Yolo Wonder) |
| Resistance to PVY Pathotype 1 | absent (Yolo Wonder, Yolo Y) |

TABLE 1-continued

Physiological and Morphological Characteristics of Line SBY28-1223

| CHARACTERISTIC | Pepper Variety SBY 28-1223 |
| --- | --- |
| Resistance to PVY Pathotype 1-2 | absent (Florida VR2, Yolo Wonder, Yolo Y) |
| Resistance to Tobacco Etch Virus | most susceptible |
| Resistance to *Phytophthora capsici* | absent/most susceptible (Yolo Wonder) |
| Resistance to Cucumber Mosaic Virus (CMV) | absent/most susceptible (Yolo Wonder) |
| Resistance to Tomato Spotted Wilt Virus (TSWV) | present (Galileo, Jackal, Jackpot) |
| Resistance to *Xanthomonas campestris pv. vesicatoria* | absent/most susceptible (Feherozon, Yolo Wonder) |
| Resistance to Anthracnose (*Gloeosporium piperatum*) | most susceptible |
| Resistance to *Cercospora* Leaf Spot (*Cercospors capsici*) | most susceptible |
| Resistance to Nematode (*Melodogyne incognita acrita*) | most susceptible |
| Resistance to Ripe Rot (*Vermicularia capsici*) | most susceptible |
| Resistance to Southern Blight (*Sclerotium rolfsii*) | most susceptible |
| Resistance to *Verticillium* Wilt (*Verticillium dahliae*) | most susceptible |

*These are typical values. Values may vary due to environment. Other values that are substantially equivalent are within the scope of the invention.

Line SBY28-1223 has been self-pollinated and planted for a number of generations to produce the homozygosity and phenotypic stability to make this line useful in commercial seed production. No variant traits have been observed or are expected for this line. Pepper line SBY28-1223, being substantially homozygous, can be reproduced by planting seeds of the line, growing the resulting pepper plant under self-pollinating or sib-pollinating conditions and harvesting the resulting seeds using techniques familiar to one of skill in the art.

C. Breeding Pepper Line SBY28-1223

One aspect of the current invention concerns methods for crossing the pepper line SBY28-1223 with itself or a second plant and the seeds and plants produced by such methods. These methods can be used for propagation of line SBY28-1223, or can be used to produce hybrid pepper seeds and the plants grown therefrom. Hybrid seeds are produced by crossing line SBY28-1223 with second pepper parent line.

The development of new varieties using one or more starting varieties is well known in the art. In accordance with the invention, novel varieties may be created by crossing line SBY28-1223 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line SBY28-1223 and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with SBY28-1223 for the purpose of developing novel sweet pepper lines, it will typically be preferred to choose those plants which either themselves exhibit one or more selected desirable characteristics or which exhibit the desired characteristic(s) when in hybrid combination. Examples of desirable traits of sweet peppers include: high seed yield, high seed germination, seedling vigor, early fruit maturity, high fruit yield, ease of fruit setting, disease tolerance or resistance, and adaptability for soil and climate conditions. Consumer-driven traits, such as a preference for a given fruit size, shape, color, texture, and taste, especially non-pungency (low capsaicinoid content), are other traits that may be incorporated into new lines of sweet pepper plants developed by this invention.

Particularly desirable traits that may be incorporated by this invention is improved resistance to different viral, fungal, and bacterial pathogens. *Anthracnose* and *Phytophthora* blight are fungal diseases affecting various species of pepper. Fruit lesions and fruit rot are the commercially important aspects of these diseases. Bacterial leaf spot and bacterial wilt are other diseases affecting pepper plants, especially during the wet season. Viral pathogens affecting pepper plants include the pepper mosaic virus and the tobacco mosaic virus.

Improved resistance to insect pests is another desirable trait that may be incorporated into new lines of pepper plants developed by this invention. Insect pests affecting the various species of pepper include the European corn borer, corn earworm, aphids, flea beetles, whiteflies, and mites (Midwest Vegetable Production Guide for Commercial Growers, 2003).

D. Performance Characteristics

As described above, line SBY28-1223 exhibits desirable agronomic traits, including resistance to Tobamovirus pathotypes P0, P1, P1-2, and P1-2-3, resistance to Tomato Spotted Wilt Virus pathotype P0, large fruits that are orange-yellow in color, and a short, compact plant. These and other performance characteristics of the line were the subject of an objective analysis of the performance traits of the line relative to other lines. The results of the analysis are presented below.

TABLE 2

Comparison of Line SBY28-1223 and a Selected Variety

|  | Line SBY28-1223 | Line Cadia (Enza Seeds) |
|---|---|---|
| Tobamovirus resistance | L4 gene - resistant to pathotypes P0, P1, P1-2, P 1-2-3 | L3 gene - resistant to pathotypes P0, P1 and P1-2 |
| PVY resistance | susceptible to pathotype P0 | resistant to pathotype P0 |
| TSWV P0 resistance | resistant | susceptible |
| Plant height | 105 cm | 145 cm |

E. Further Embodiments of the Invention

In particular embodiments, the invention provides plants of pepper line SBY28-1223 modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those pepper plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental pepper plant which contributes the locus for the desired characteristic is termed the nonrecurrent or donor parent. This terminology refers to the fact that the nonrecurrent parent is used one time in the backcross protocol and therefore does not recur. The parental pepper plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then crossed again to the recurrent parent and the process is repeated until a pepper plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny pepper plants of a backcross in which SBY28-1223 is the recurrent parent comprise (i) the desired trait from the non-recurrent parent and (ii) all of the physiological and morphological characteristics of pepper line SBY28-1223 as determined at the 5% significance level when grown in the same environmental conditions.

Pepper varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the downy mildew resistance trait. For this selection process, the progeny of the initial cross are sprayed with downy mildew spores prior to the backcrossing. The spraying eliminates any plants which do not have the desired downy mildew resistance characteristic, and only those plants which have the downy mildew resistance gene are used in the subsequent backcross. This process is then repeated for all additional backcross generations.

Selection of pepper plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of pepper are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived From Pepper Line SBY28-1223 by Genetic Engineering

Many useful traits that can be introduced by backcrossing, as well as directly into a plant, are those which are introduced by genetic transformation techniques. Genetic transformation may therefore be used to insert a selected transgene into the pepper line of the invention or may, alternatively, be used for the preparation of transgenes which can be introduced by backcrossing. Methods for the transformation of plants, including pepper plants, are well known to those of skill in the art (see, e.g., below). Techniques which may be employed for the genetic transformation of pepper plants include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

*Agrobacterium*-mediated transformation of pepper explant material and regeneration of whole transformed pepper plants (including tetraploids) from the transformed shoots has been shown to be an efficient transformation method (U.S. Pat. No. 5,262,316).

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target pepper cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modem *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for pepper plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunI, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the pepper lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a pepper plant according to the invention. Non-limiting examples of particular genes and corresponding phenotypes one may choose to introduce into a pepper plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a pepper variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a pepper plant by transformation.

H. Deposit Information

A deposit of pepper line SBY28-1223, disclosed above and recited in the claims, has been made with the American Type Culture Collection (ATCC), 10801 University Blvd., Manassas, Va. 20110-2209. The date of deposit was May 30, 2008. The accession number for those deposited seeds of pepper line SBY28-1223 is ATCC Accession No. PTA-9226. Upon issuance of a patent, all restrictions upon the deposit will be removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,262,316
U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 7,087,819
An et al., *Plant Physiol.*, 88:547, 1988.
Berke, *J. New Seeds*, 1:3-4, 1999.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Chae et al., *Capsicum Eggplant Newsltr.*, 22:121-124, 2003.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125,1997
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Midwest Veg. Prod. Guide for Commercial Growers (ID:56), 2003
Odel et al., *Nature*, 313:810, 1985.
Omirulleh et al., *Plant Mol. Biol.*, 21(3):415-428, 1993.
Pandal et al., *Theor. Appl. Gene.*, 68(6):567-577, 1984.
Pickersgill and Barbara, *Euphytica*, 96(1):129-133, 1997
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
PCT Appln. No. WO 99/31248

What is claimed is:

1. A seed of pepper line SBY28-1223, a sample of seed of said line having been deposited under ATCC Accession Number PTA-9226.

2. A plant grown from the seed of claim 1.

3. A plant part of the plant of claim 2.

4. The plant part of claim 3, wherein said part is selected from the group consisting of a fruit, pollen, rootstock, scion, an ovule and a cell.

5. A pepper plant, or a part thereof, having all the physiological and morphological characteristics of the pepper plant of claim 2.

6. A tissue culture of regenerable cells of pepper line SBY28-1223, a sample of seed of said line having been deposited under ATCC Accession Number PTA-9226.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A pepper plant regenerated from the tissue culture of claim 6, wherein the regenerated plant expresses all of the physiological and morphological characteristics of pepper line SBY28-1223, a sample of seed of said line having been deposited under ATCC Accession Number PTA-9226.

9. A method of producing pepper seed, comprising crossing the plant of claim 2 with itself or a second pepper plant.

10. The method of claim 9, wherein the plant of pepper line SBY28-1223 is the female parent.

11. An F1 hybrid seed produced by the method of claim 9, wherein the pepper plant of line SBY28-1223 is crossed with a distinct second pepper plant.

12. An F1 hybrid plant produced by growing the seed of claim 11.

13. A method for producing a seed of a line SBY28-1223-derived pepper plant comprising the steps of:
(a) crossing a pepper plant of line SBY28-1223, a sample of seed of said line having been deposited under ATCC Accession Number PTA-9226, with a second pepper plant; and
(b) allowing seed of a SBY28-1223-derived pepper plant to form.

14. The method of claim 13, further comprising the steps of:
(c) crossing a plant grown from said SBY28-1223-derived pepper seed with itself or a second pepper plant to yield additional SBY28-1223-derived pepper seed;

(d) growing said additional SBY28-1223-derived pepper seed of step (c) to yield additional SBY28-1223-derived pepper plants; and (e) repeating the crossing and growing steps of (c) and (d) to generate further SBY28-1223-derived pepper plants.

15. A method of vegetatively propagating a plant of pepper line SBY28-1223 comprising the steps of:
    (a) collecting tissue capable of being propagated from a plant of pepper line SBY28-1223, a sample of seed of said line having been deposited under ATCC Accession Number PTA-9226;
    (b) cultivating said tissue to obtain proliferated shoots; and
    (c) rooting said proliferated shoots to obtain rooted plantlets.

16. The method of claim 15, further comprising growing plants from said rooted plantlets.

17. A method of introducing a desired trait into pepper line SBY28-1223 comprising:
    (a) crossing a plant of line SBY28-1223, a sample of seed of said line having been deposited under ATCC Accession Number PTA-9226, with a second pepper plant that comprises a desired trait to produce F1 progeny;
    (b) selecting an F1 progeny that comprises the desired trait;
    (c) crossing the selected F1 progeny with a plant of line SBY28-1223, a sample of seed of said line having been deposited under ATCC Accession Number PTA-9226, to produce backcross progeny;
    (d) selecting backcross progeny comprising the desired trait and the physiological and morphological characteristic of pepper line SBY28-1223; and
    (e) repeating steps (c) and (d) three or more times in succession to produce selected fourth or higher backcross progeny that comprise the desired trait.

18. A pepper plant produced by the method of claim 17.

19. A method of producing a plant of pepper line SBY28-1223, a sample of seed of said line having been deposited under ATCC Accession Number PTA-9226, comprising an added desired trait, the method comprising introducing a transgene conferring the desired trait into a plant of pepper line SBY28-1223.

20. A progeny plant of the plant of claim 2, which progeny comprises all of the physiological and morphological characteristics of pepper line SBY28-1223, a sample of seed of said line having been deposited under ATCC Accession Number PTA-9226.

21. A seed that produces the plant of claim 20.

22. A method of determining the genotype of the plant of claim 2, comprising obtaining a sample of nucleic acids from said plant and detecting in said nucleic acids a plurality of polymorphisms.

23. The method of claim 22, further comprising the step of storing the results of the step of detecting the plurality of polymorphisms on a computer readable medium.

24. A method of producing peppers comprising:
    (a) obtaining the plant of claim 2, wherein the plant has been cultivated to maturity; and
    (b) collecting peppers from the plant.

\* \* \* \* \*